(12) United States Patent
Saija

(10) Patent No.: US 10,473,570 B2
(45) Date of Patent: Nov. 12, 2019

(54) CONTROL SOLUTION FOR SELF-HEALING MATERIALS

(71) Applicant: Telia Company AB, Solna (SE)

(72) Inventor: Timo Saija, Espoo (FI)

(73) Assignee: Telia Company AB, Solna (SE)

( * ) Notice: Subject to any disclaimer, the term of this patent is extended or adjusted under 35 U.S.C. 154(b) by 405 days.

(21) Appl. No.: 15/196,161

(22) Filed: Jun. 29, 2016

(65) Prior Publication Data

US 2017/0010195 A1 Jan. 12, 2017

(30) Foreign Application Priority Data

Jul. 6, 2015 (FI) ...................................... 20155536

(51) Int. Cl.
  *G01N 3/08* (2006.01)
  *B29C 73/22* (2006.01)
  *G01N 3/60* (2006.01)
  *B29C 35/02* (2006.01)

(52) U.S. Cl.
  CPC ............... *G01N 3/08* (2013.01); *B29C 73/22* (2013.01); *G01N 3/60* (2013.01); *B29C 35/0272* (2013.01)

(58) Field of Classification Search
  USPC .......................................................... 702/35
  See application file for complete search history.

(56) References Cited

U.S. PATENT DOCUMENTS

| 8,518,703 | B1 | 8/2013 | Wright |
| 2009/0210083 | A1* | 8/2009 | English ................ G06Q 10/087 700/109 |
| 2009/0294022 | A1 | 12/2009 | Hayes et al. |
| 2011/0023611 | A1 | 2/2011 | Jones et al. |
| 2014/0186476 | A1 | 7/2014 | Hemmelgarn et al. |
| 2015/0168343 | A1 | 6/2015 | Hayashita et al. |

OTHER PUBLICATIONS

Finnish Search Report dated Jan. 2, 2016, in corresponding Finland Application 20155536.
Hurley et al., "Coordinated sensing and active repair for self-healing", Smart Material and Structures, vol. 20, No. 2, Jan. 14, 2011, pp. 1-7, School of Engineering, University of Vermont, Burlington, VT.
Leng et al., "Shape-memory polymers and their composites: Stimulus methods and applications", Progress in Materials Science, vol. 56, Issue 7, pp. 1077-1135, Sep. 2011, Harbin Institute of Technology (HIT), Harbin, PR China.

* cited by examiner

*Primary Examiner* — Paul D Lee
(74) *Attorney, Agent, or Firm* — Young & Thompson

(57) ABSTRACT

A method for controlling a repair of at least one non-autonomic extrinsic self-healing material in an object, the method including: triggering, by a server, at least one sensor element embedded in the at least one non-autonomic extrinsic self-healing material to initiate a testing procedure, receiving a result of the testing procedure, analyzing the result, determining capability information of the sensor element with an inquiry, receiving the capability information, determining a triggering instruction to the sensor element on the basis of the capability information, delivering the triggering instruction to utilize an applicable capability of the sensor element to the sensor element. A server implementing the method and a system are also described.

11 Claims, 3 Drawing Sheets

CONTROL SOLUTION FOR SELF-HEALING MATERIALS

TECHNICAL FIELD

The invention concerns in general the technical field of communication solutions. Especially the invention concerns control solutions arranged by means communication technology within an area of self-healing materials.

BACKGROUND

The development in an area of so called self-healing materials has paved a way to implement further solutions in the area. The self-healing materials are a class of smart materials that have a structurally incorporated ability to repair damage developed in the material in one way or another. Some self-healing materials, known as non-autonomic extrinsic self-healing materials, are such that in order to initiate a repair process an external triggering shall be provided to the material. The external triggering may e.g. be a provision of additional light, heat, laser beam, radiation or electricity to the material element. A non-limiting example of a non-autonomic extrinsic self-healing material is polymeric nanoparticles.

In case that a structure, i.e. an object, is manufactured from multiple non-autonomic extrinsic self-healing materials it is necessary to manage and control an initiation and operation of the repair process. Hence, there is need to develop solution by means of which it is possible to control the repair process of said self-healing materials in an optimal manner.

SUMMARY

An objective of the invention is to present a method, a server and a system for controlling a repair of at least one non-autonomic extrinsic self-healing material in an object. Another objective of the invention is that the method, the server and the system provide an optimized self-healing process through the controlling.

The objectives of the invention are reached by a method, a server and a system as defined by the respective independent claims.

According to a first aspect, a method for controlling a repair of at least one non-autonomic extrinsic self-healing material in an object is provided wherein the method comprises: triggering, by a server, at least one sensor element embedded in the at least one non-autonomic extrinsic self-healing material to initiate a testing procedure for the at least one non-autonomic extrinsic self-healing material; receiving a result of the testing procedure in the server; analysing the result of the testing procedure; determining capability information of the sensor element with an inquiry; receiving the capability information in the server; determining a triggering instruction to the sensor element in the server on the basis of the capability information; delivering the triggering instruction to utilize an applicable capability of the sensor element to the sensor element.

The triggering instruction may further comprise an instruction for re-triggering the testing procedure. The instruction for re-triggering the testing procedure may also comprise a time value for a timer implemented in the sensor element. The time value may be dependent on the predetermined repair process.

According to a second aspect, a server for controlling a repair of at least one non-autonomic extrinsic self-healing material in an object is provided, the server comprises at least one processor, and at least one memory storing at least one portion of computer program code, wherein the processor being configured to cause the server at least to perform: trigger at least one sensor element embedded in the at least one non-autonomic extrinsic self-healing material to initiate a testing procedure for the at least one non-autonomic extrinsic self-healing material; receive a result of the testing procedure; analyse the result of the testing procedure; determine capability information of the sensor element with an inquiry; receive the capability information; determine a triggering instruction to the sensor element on the basis of the capability information; deliver the triggering instruction to utilize an applicable capability of the sensor element to the sensor element.

The server may be configured to add an instruction for re-triggering the testing procedure in the triggering instruction. The server may also be configured to add a time value for a timer implemented in the sensor element in the instruction for re-triggering the testing procedure. The time value may be dependent on the predetermined repair process.

According to a third aspect, a system for controlling a repair of at least one non-autonomic extrinsic self-healing material in an object is provided, the system comprising: at least one sensor element embedded in at least one non-autonomic extrinsic self-healing material in an object, and a server configured at least to perform: trigger the at least one sensor element embedded in the at least one non-autonomic extrinsic self-healing material to initiate a testing procedure, by the at least one sensor element, for the at least one non-autonomic extrinsic self-healing material; receive a result of the testing procedure from the at least one sensor element; analyse the result of the testing procedure; determine capability information of the sensor element with an inquiry; receive the capability information; determine a triggering instruction to the sensor element on the basis of the capability information; deliver the triggering instruction to utilize an applicable capability of the sensor element to the sensor element.

The system may further comprise an intermediate terminal configured to operate as a link between the server and the at least one sensor element.

Alternatively or in addition, the intermediate terminal may be configured to perform at least some of the functions of the server.

The exemplary embodiments of the invention presented in this patent application are not to be interpreted to pose limitations to the applicability of the appended claims. The verb "to comprise" is used in this patent application as an open limitation that does not exclude the existence of also un-recited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objectives and advantages thereof, will be best understood from the following description of specific embodiments when read in connection with the accompanying drawings.

BRIEF DESCRIPTION OF FIGURES

The embodiments of the invention are illustrated by way of example, and not by way of limitation, in the figures of the accompanying drawings.

DESCRIPTION OF SOME EMBODIMENTS

Figure 1:
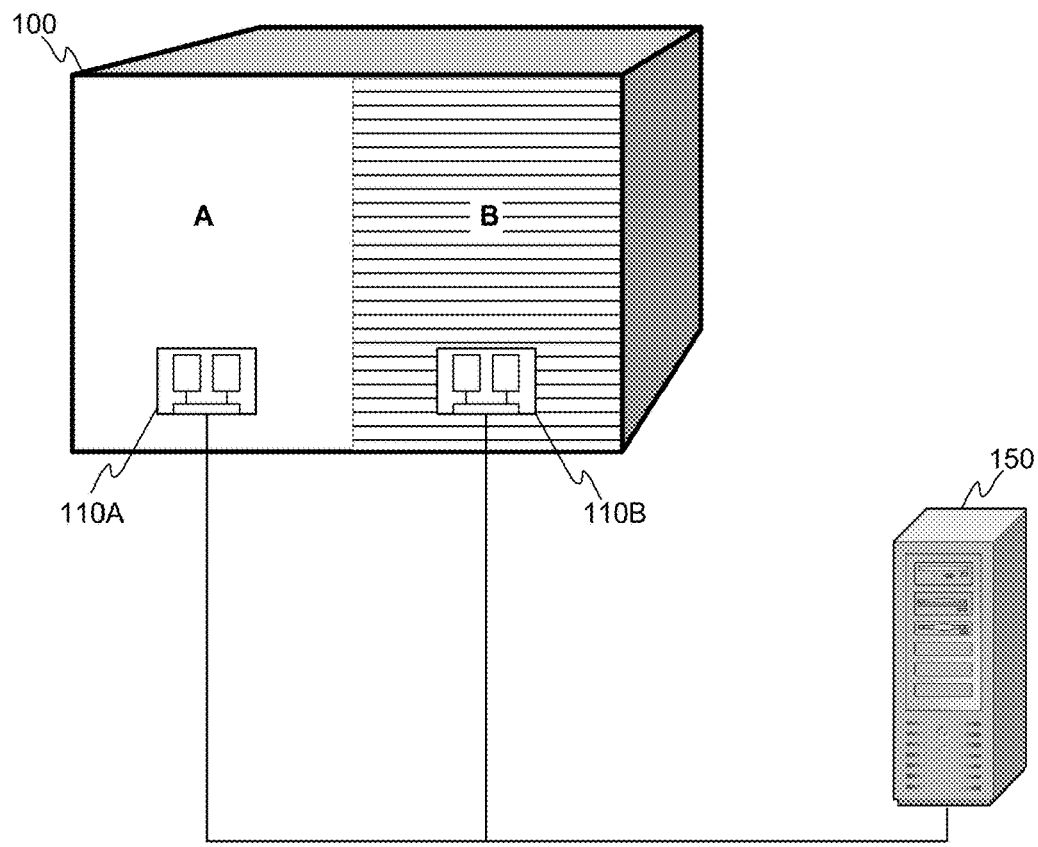
FIG. 1 illustrates schematically an example of an environment in which the invention is implemented.

FIG. 1 discloses a non-limiting example of an environment in which the invention may be implemented. In the environment an object 100 comprising at least two different non-autonomic extrinsic self-healing materials (marked with A and B in FIG. 1). The object 100 may be some sort of structure in a building, for example. One or more sensor elements 110A, 110B are embedded in the object so that at least one sensor element 110A, 110B is embedded in the non-autonomic extrinsic self-healing material to be monitored. The embedding may advantageously be implemented so that the sensor element 110A, 110B is capable of performing tasks as will be discussed in the following. The sensor elements 110A, 110B are communicatively coupled to a server 150.

Figure 2:
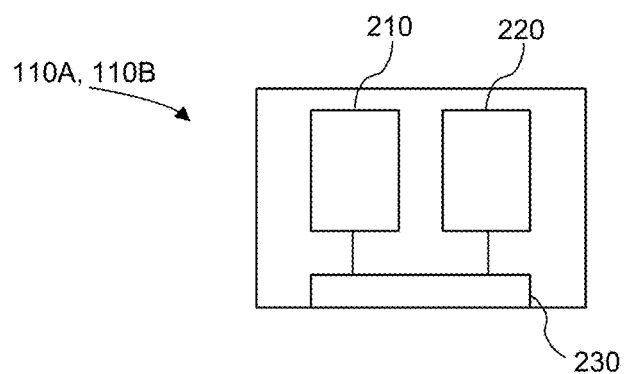
FIG. 2 illustrates schematically in an exemplified manner a sensor element according to an embodiment of the invention.

FIG. 2 illustrates in an exemplified manner a sensor element 110A, 110B according to an embodiment of the invention. The sensor element 110A, 110B comprises at least one sensor device 210, at least one actuating device 220 and at least one communication device 230, such as a wired or wireless modem. The sensor device 210 may comprise one or more sensors, which is configured to obtain predetermined information on the material to be measured. The predetermined information may e.g. be any parameter by means of which it is possible to determine if there is a defect in the material monitored or not. For example, the sensor device 210 may be a strain gauge configured to obtain information on a tension of the object to be measured. A change in tension may, for example, indicate that there is a crack in the object. The actuating device 220, in turn, may be a device which is capable of providing at least one type of external triggering to the material in question in order to initiate the self-healing process to the detected defect if possible. The external trigger may e.g. be light, heat, radiation or electricity provided to the material. Some simple non-limiting examples of the actuating device are led (light emitting diodes) or heat resistance. The communication device may be, as already mentioned, a wired or wireless modem performing operations by means of which the sensor element may communication internally and externally. The internal communication refers to a communication between the mentioned devices within the sensor element. External communication refers to a communication with the server 150. The sensor element 110A, 110B as illustrated in FIG. 2 does not disclose any separate processing unit for managing and controlling the operation of the sensor element, but it may comprise such a separate unit or such an operation may be integrated in any of the described devices.

Figure 3:
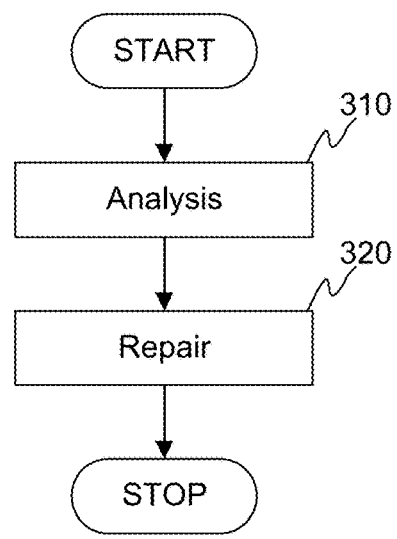
FIG. 3 illustrates schematically a principle of the method according to an embodiment of the invention.

FIG. 3 illustrates schematically a principle of the method according to an embodiment of the invention. The method comprises two stages wherein the first stage 310 is an analysis stage and the second stage is a repair stage 320. In the analysis stage 310 information is obtained from the sensor element and it is analysed. Based on the analysis a repair process related actions are performed in the repair stage 320.

Figure 4:
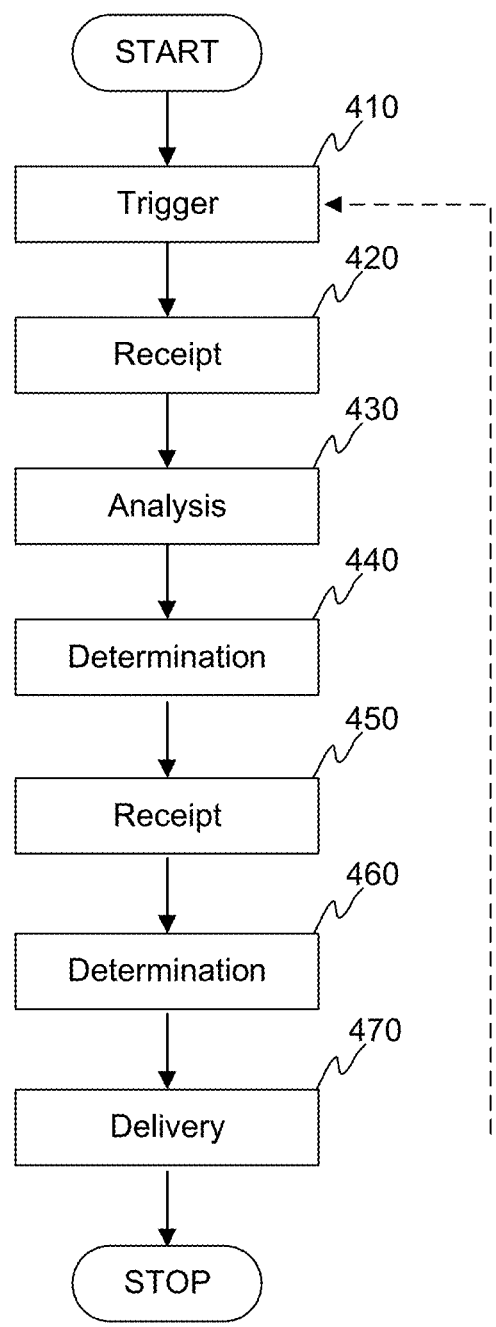
FIG. 4 illustrates schematically an example of the method according to an embodiment of the invention in more detail.

FIG. 4 illustrates schematically an example of the method according to an embodiment of the invention as a flow chart in more detail. The method is described from the server 150 point of view and it relates to a controlling of a repair of at least one non-autonomic extrinsic self-healing material in an object comprising multiple non-autonomic extrinsic self-healing materials. In the method the server 150 is configured to trigger 410 at least one sensor element embedded in the at least one non-autonomic extrinsic self-healing material to initiate a testing procedure for the at least one non-autonomic extrinsic self-healing material. The testing procedure is performed in the sensor element and a result of the testing procedure, i.e. obtained measurement results from the sensor device, is received, which result is transmitted to the server 150 with a message. In response to a receipt 420 of the result of the testing procedure in the server 150, the result of the testing procedure is analysed 430 in the server 150. The server may be configured to extract the measurement result or results from the received message and compare it to a reference value or values, which is stored in the server 150, or at least accessible by it. The reference value may be a theoretical value characteristic to the material in question or a previous measurement result, for instance. In order to determine a correct reference value the message may comprise an identifier for identifying a sensor element or sensor device in order to obtain an applicable reference value for the comparison. Alternatively analysis may apply such values which were previously used successfully, deviating from predetermined reference value. The previous examples of the analysis are not limiting and the analysis may be performed in any other way than described. In response to a detection that there is need to initiate a repair process of the at least one non-autonomic extrinsic self-healing material, the server 150 is configured to determine 440 what kind of repair process the sensor element may initiate through triggering. In other words, the aim of this step is to find out if the sensor element is capable of initiating a required repair process or not when there is need for such. The determination may be either performed by inquiring it from the sensor element 110A, 110B or by initiating a query to a database storing the information. In response to the receipt 450 of the capability information of the sensor element 110A, 110B the server 150 is configured to determine 460 an applicable triggering instruction to the sensor element. The determination may comprise at least adjustment value, such as time or power parameter, for at least one actuating device residing in the sensor element. Alternatively or in addition, it may comprise a determination of an actuating device, which is to be triggered in order to initiate the repair process. Naturally, the determination of the triggering instruction is at least partly dependent on the material in question. When the triggering instruction, i.e. necessary parameters, are determined by the server 150, the server 150 may control the sensor element to operate accordingly by delivering instruction 470 to the sensor element in order to initiate a repair process in the non-autonomic extrinsic self-healing material in question by activating an applicable capability of the sensor element in question. The triggering instruction may e.g. be delivered in a predetermined message configured to transfer information either directly or indirectly between the server 150 and the sensor element 110A, 110B and any devices within the mentioned entities.

In case that the server receives measurement results from multiple sensor elements, either embedded in the same material or in the different materials, the analysis 430 may provide information which one of the possible detections is the most critical and provide to it a higher priority than to the others. This may be implemented by determining which one of the measurement results deviates most from the reference value. Alternatively or in addition, it may be determined which one of the deviations is the most critical on a basis of some stored information. In such a case the determination step 460 of determining a triggering instruction may comprise a feature in which the triggering instruction is determined for the most critical detection, at least in a first place.

In some implementation of the present invention the triggering instruction delivered to the sensor element 110A, 110B may comprise an instruction to re-triggering the testing procedure in the sensor element in question, or multiple sensor elements embedded in the object. This is advantageous in a sense that it is possible to detect immediately if the repair process has been successful or if the process shall be repeated. The delivery of the re-triggering instruction is depicted with dashed arrow line in FIG. 4.

Moreover, the server 150 may be configured to determine, from e.g. stored information accessible by the server 150, a time value for a timer configured to delay the re-triggering of the testing procedure. The time value may e.g. be dependent on the instructed repair process. The timer may be executed either in the server or in the sensor element in which case the time value is delivered to the sensor element. By means of the timer it is possible to adjust an optimal point of time when the testing procedure shall be re-initiated in order to see any effect of the previous repair process in the material.

Figure 5:
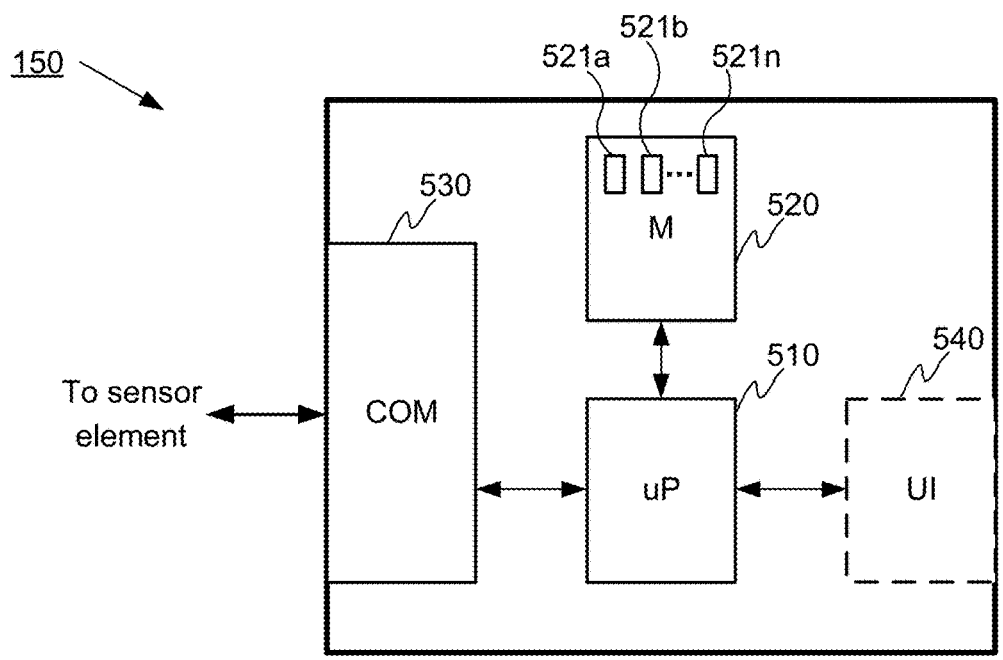
FIG. 5 illustrates schematically an example of a server according to an embodiment of the invention.

FIG. 5 discloses an example of a server 150 according to an embodiment of the invention. The server 150 may comprise one or more processors 510, one or more memories 520 being volatile or non-volatile for storing portions of computer program code 521a-521n and any data values, a communication interface 530 and possibly one or more user interface units 540. The mentioned elements are communicatively coupled to each other with e.g. an internal bus. The communication interface provides interface for communication with any external unit, such as with one or more network nodes, one or more data storages, one or more mobile terminals, for example. The communication interface is based on one or more known communication technologies, either wired or wireless, in order to communicate with an external unit in question.

The processor 510 of the server 150 is at least configured to implement the method as described. The implementation of the method may be achieved by arranging the processor 510 to execute at least some portion of computer program code 521a-521n stored in the memory 520 causing the processor 510, and thus the server 150, to implement one or more method steps as described. Hence, the processor 510 is arranged to access the memory 520 and retrieve and store any information therefrom and thereto. Moreover, the processor 510 is configured to control the communication through the communication interface 530 with any external unit. The processor 510 may also be configured to control the output of information, i.e. data. The processor 510 may also be configured to control storing of received and delivered information as well as processing it. For sake of clarity, the processor herein refers to any unit suitable for processing information and control the operation of the server, among other tasks. The mentioned operations may e.g. be implemented with a microcontroller solution with embedded software. Similarly, the invention is not limited to a certain type of memory only, but any memory type suitable for storing the described pieces of information may be applied in the context of the present invention.

In the previous description of the invention it is mainly discussed on an implementation in which a server 150 is arranged to communicate with one or more sensor elements 110A, 110B embedded in an object to be monitored. The present invention may also be implemented in such a manner that there is an intermediate terminal operating between the server 150 and the sensor element(s) 110A, 110B. The intermediate terminal is advantageously equipped with necessary hardware and software implementation in order to perform the tasks required. The intermediate terminal may, for example, be configured to trigger the testing procedure of the sensor element by communicating with the sensor element in question. The triggering may be implemented with some short range communication method, such as Bluetooth. In other words, both the intermediate terminal and the sensor element or sensor elements are equipped with the short range communication devices and the intermediate device may be configured to trigger the testing procedure. Furthermore, the intermediate terminal may be configured to operate as a link to the server, or even to perform at least some part of the analysis, in order to determine if the repair process shall be initiated or not. In some implementation the intermediate device may be instructed to trigger the capability of the sensor element e.g. with the short range communication with the sensor element. This may be in response to an instruction from the server, especially if the server performs the analysis, or at least part of it. Other variations are also available in the utilization of an intermediate device in the method according to the present invention.

The invention relates also to a system in which the server and at least one sensor element are communicatively coupled to perform the method as described. In some implementation the system may comprise an intermediate terminal configured to operate as a link between the server and the at least one sensor element. Moreover, in some further implementation the intermediate terminal may perform at least some of the functions of the server, e.g. as described above.

Features described in the preceding description may be used in combinations other than the combinations explicitly described. Although functions have been described with reference to certain features, those functions may be performable by other features whether described or not. Although features have been described with reference to certain embodiments, those features may also be present in other embodiments whether described or not.

The invention claimed is:

1. A method for controlling a repair of at least one non-autonomic extrinsic self-healing material in an object, the method comprising:
   triggering, by a server, at least one sensor element embedded in the at least one non-autonomic extrinsic self-healing material to initiate a testing procedure for the at least one non-autonomic extrinsic self-healing material;
   receiving a result of the testing procedure in the server;
   analyzing the result of the testing procedure, in the server;
   determining capability information of the sensor element with an inquiry;
   receiving the capability information in the server;
   determining a triggering instruction to the sensor element in the server based on the capability information; and
   delivering, from the server, the triggering instruction to utilize an applicable capability of the sensor element to the sensor element, the triggering instruction delivered to the sensor element triggering a repair process of the self-healing material.

2. The method of claim 1, wherein the triggering instruction further comprises an instruction for re-triggering the testing procedure.

3. The method of claim 2, wherein the instruction for re-triggering the testing procedure comprises a time value for a timer implemented in the sensor element.

4. The method of claim 3, wherein the time value is dependent on a predetermined repair process.

5. A server for controlling a repair of at least one non-autonomic extrinsic self-healing material in an object, the server comprising:
at least one processor; and
at least one memory storing at least one portion of computer program code,
wherein the processor is configured to cause the server at least to:
trigger at least one sensor element embedded in the at least one non-autonomic extrinsic self-healing material to initiate a testing procedure for the at least one non-autonomic extrinsic self-healing material,
receive a result of the testing procedure,
analyze the result of the testing procedure,
determine capability information of the sensor element with an inquiry,
receive the capability information,
determine a triggering instruction to the sensor element based on the capability information, and
deliver the triggering instruction to utilize an applicable capability of the sensor element to the sensor element, the triggering instruction delivered to the sensor element triggering a repair process of the self-healing material.

6. The server of claim 5, wherein the processor is configured to cause the server to add an instruction for re-triggering the testing procedure in the triggering instruction.

7. The server of claim 6, wherein the processor is configured to cause the server to add a time value for a timer implemented in the sensor element in the instruction for re-triggering the testing procedure.

8. The server of claim 7, wherein the time value is dependent on a predetermined repair process.

9. A system for controlling a repair of at least one non-autonomic extrinsic self-healing material in an object, the system comprising:
at least one sensor element embedded in at least one non-autonomic extrinsic self-healing material in an object; and
a server configured at least to:
trigger the at least one sensor element embedded in the at least one non-autonomic extrinsic self-healing material to initiate a testing procedure, by the at least one sensor element, for the at least one non-autonomic extrinsic self-healing material,
receive a result of the testing procedure from the at least one sensor element,
analyze the result of the testing procedure,
determine capability information of the sensor element with an inquiry,
receive the capability information,
determine a triggering instruction to the sensor element based on the capability information, and
deliver the triggering instruction to utilize an applicable capability of the sensor element to the sensor element, the triggering instruction delivered to the sensor element triggering a repair process of the self-healing material.

10. The system of claim 9, further comprising an intermediate terminal configured to operate as a link between the server and the at least one sensor element.

11. The system of claim 10, wherein the intermediate terminal is configured to perform at least some of the functions of the server.

* * * * *